United States Patent [19]

Abraham et al.

[11] 4,413,506
[45] Nov. 8, 1983

[54] HORIZONTAL FILM BALANCE HAVING WIDE RANGE AND HIGH SENSITIVITY

[75] Inventors: Bernard M. Abraham, Oak Park; Kenjiro Miyano, Downers Grove; John B. Ketterson, Evanston, all of Ill.

[73] Assignee: The United States of America as represented by the U.S. Department of Energy, Washington, D.C.

[21] Appl. No.: 240,647

[22] Filed: Mar. 5, 1981

[51] Int. Cl.³ .......................................... G01N 13/02
[52] U.S. Cl. ...................................................... 73/64.4
[58] Field of Search ......................................... 73/64.4

[56] References Cited

PUBLICATIONS

Buzard, K. et al., *A Wide Range High Sensitivity Film Balance* Rev. Sci. Instrum. vol. 51, No. 8, (Aug. 1980), pp. 1083–1087.
Albrecht, O. et al., *A Precision Langmuir Film Balance System*, J. Phys. E. Sci. Instrum. vol. 13, No. 5, (May 1980), pp. 512–515.
Langmuir, I., *The Constitution and Fundamental Properties of Solids and Liquids, II Liquids*, vol. 39, (May 23, 1917), pp. 1848–1872.
Pagano, R. E., et al., *A Millidyne Film Balance for Measuring Intermolecular Energies in Lipid Films*, Jour. of Coll. and Interface Sci. vol. 41, No. 2, (Nov. 1972), pp. 311–317.
Tabak, S. A., et al., *Modified Technique for Dynamic Surface Pressure and Relaxation Measurements at the Air-Water Interface*, Rev. of Sci. Instrum. vol. 48, No. 9, (Sep. 1977), pp. 1196–1201.
Stenberg, M. et al., *A New Instrument for Measuring Surface Pressure*, Rev. Sci. Instrum. vol. 50, No. 9, (Sep. 1979), pp. 1098–1100.
Vroman, L. et al., *Surface Film Pressure Recording System*, (Periodical unknown), (Oct. 1967), pp. 278–279.
Trurnit, H. J. et al., *Automatic Recording Film Balance System*, Rev. Sci. Instrum. vol. 30, No. 11, (Nov. 1959), pp. 975–981.
Adam, N. K., *The Properties and Molecular Structure of Thin Films of Palmitic Acid on Water, Parts I & II*, Royal Society Proceed., Series A, vols. 99 and 110, (Mar. 1921 and May 1922), pp. 336–351 and 452–472.
Harkins, W. D. et al., *I. A Simple Accurate Film Balance of the Vertical Type for Biological & Chemical Work, and a Theoretical and Experimental Comparison with the Horizontal Type*, (Periodical Unknown), vol. 59, (1937), pp. 2189–2197.
Hawkins, G. A., et al. *Measurements of the Equation of State of a Two-Dimensional Gas Near its Critical Point*, Phys. Rev. Letters, vol. 32, No. 10, (Mar. 1974), pp. 524–527.
Harkins, W. D. et al., *Contact Potentials and the Effects of Unimolecular Films on Surface Potentials, I. Films of Acids and Alcohols*, Journ. of Chem. Phy., vol. I, (Dec. 1933), pp. 852–862.
Adam, N. K. et al., *The Structure of Thin Films, Part VII*, Royal Soc. Proceed., Series A. vol. 110, (1925), pp. 423–441.
Fromherz, P., *Instrumentation for Handling Monomolecular Films at an Air-Water Interface*, Rev. Sci. Instrum. vol. 46, No. 10, (Oct. 1975), pp. 1380–1385.

*Primary Examiner*—E. R. Kazenske
*Assistant Examiner*—Joseph W. Roskos
*Attorney, Agent, or Firm*—Bruce R. Mansfield; Paul A. Gottlieb; Richard G. Besha

[57] ABSTRACT

A thin-film, horizontal balance instrument is provided for measuring surface tension (surface energy) of thin films suspended on a liquid substrate. The balance includes a support bearing and an optical feedback arrangement for wide-range, high sensitivity measurements. The force on the instrument is balanced by an electromagnet, the current through the magnet providing a measure of the force applied to the instrument. A novel float construction is also disclosed.

10 Claims, 5 Drawing Figures

HORIZONTAL FILM BALANCE HAVING WIDE RANGE AND HIGH SENSITIVITY

CONTRACTUAL ORIGIN OF THE INVENTION

The U.S. Government has rights in this invention pursuant to Contract No. W-31-109-ENG-38 between the U.S. Department of Energy and Argonne National Laboratory.

BACKGROUND OF THE INVENTION

This invention pertains to film balances of the type used to measure the surface tension or surface energy of a thin film. More particularly, this invention pertains to such balances of the Langmuir or horizontal type, as distinguished from balances of the Wilhelmy or vertical type. In the Langmuir balance, an elongated horizontal trough is filled with a liquid substrate, usually water. A barrier spanning the width of the trough separates the upper surface of the substrate into two portions. The thin film to be investigated, usually an oil or the like, is formed on one side of the barrier by depositing a small amount of film material, or a mixture of film material and volatile solvent, on the surface of the substrate. The film material then spreads out from the point of deposit, forming a monolayer thin film on the surface of the substrate. The surface area of the coated substrate portion is then reduced, reducing the area of the thin film to be studied, and compressing the thin film against the aforementioned barrier. A force is, in this manner, exerted upon the side of the barrier contacting the thin film. Inasmuch as the opposing side of the barrier bounds a surface of uncoated substrate, a surface energy (surface tension) differential is set up on the barrier. Prior art barriers were typically very thin, comprising paraffin-coated paper and the like, and floated on the clean uncoated surface, so as to be capable of movement under the force of the thin film which was compressed against one side of the barrier. The movement of the barrier, more commonly termed a float, upon the horizontal substrate surface was detected by knife-edge or torsion wire movements which were attached to the float by vertical members extending normal to the substrate surface. However, difficulties were experienced with both types of movements. The earliest film balance in use today was reported by Langmuir in 1921. In that arrangement, the float was mounted from above for pivotal deflection, by a knife-edge movement. One side of the knife-edge movement was attached through a transverse horizontally extending arm to a weight pan, to form one-half of a scale, the weight in the pan balancing the pivotal deflection of the knife edge, caused by the differential surface energy applied to the float. Such arrangements were quickly discarded in favor of the second, torsion wire type, when the instability of the knife edge proved to detrimental to more accurate measurements. The knife edge movement proved unsatisfactory in that the forces applied to the knife edge which caused it to rock, could if large enough, cause the knife edge to slide horizontally, destroying the zero set and measuring ability of the device. The knife edge movement presented further problems in that, if tilted too far from a balanced vertical position, would become unable to support itself, causing the knife edge to fall to one side, again destroying the zero set and measuring ability of the mechanism. Knife-edge movements also display a dead region adjacent a vertical or balanced orientation, thereby defining a minimum deflection limit of the useful operating range of such a balancing mechanism.

The second type of balance, currently in use today suspends the float from torsion wire movement, wherein the horizontal deflection of the float is transformed into a torsion force which rotatably deflects the torsion wire from which it is suspended. While overcoming the instability problems of the knife-edge mechanism, this arrangement suffers from its own peculiar drawbacks. In order to provide the high sensitivity currently required of such balances, the torsion wire must be made as lightweight as possible. However, as the guage of the torsion wire is reduced, its ability to support massive float mechanisms is also reduced. Accordingly, only very light float arrangements can be used with this the torsion-type measurement device.

Further difficulties were encountered in prior art float constructions which were known to swamp at high differential surface tensions, thus permitting thin film material to leak past their end portions, thereby destroying measurement accuracy.

It is therefore an object of the present invention to provide a thin film balance having improved sensitivity while providing the support necessary to suspend more massive floats as well as associated measuring equipment.

It is a further object of the present invention to provide a highly sensitive film balance having a wide range measuring capability. The film balance having such wide range capability must be conveniently operable over its entire operating range, without requiring breakdown or set-up of various portions of the film balance mechanism.

Another object of the present invention is to provide an improved float for a film balance, which is resistant or virtually unaffected by swamping at high differential forces. Such float must also present an impassable barrier to the thin film under examination, i.e., thin film material must not be allowed to leak past the ends of the float.

It is yet another object of the present invention to provide a film balance having the advantages set forth above, which further provides a highly accurate automated balancing means.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

These and other objects of the present invention are provided in a thin film balance having a horizontal trough which as divided in first and second portions by a movable barrier or float. A liquid substrate is then disposed within first and second portions of the trough. A thin film is floated upon the substrate surface of the first substrate portion, which is bounded on one side by the float. A movable barrier bounding a second side of the thin film is then moved toward the float, compressing the surface area of the substrate upon which the thin film resides. During such compression of the thin film, a force is transmitted along one side of the float. The float is suspended, through vertical support members, to a jeweled pivotal mechanism which allows the float to be deflected under the aforementioned force of the compressed thin film. A horizontally extending arm, joined to the jeweled pivot mechanism, contains a variable weight device at one end and an optical feedback positioning device at the other end. When the float is deflected under force of the compressed thin film, the horizontal arm rotates in a vertical plane with the second end of the horizontal arm passing through the optical transmission path of the optical feedback positioning system. A magnetic coil is attached adjacent the second end of the horizontal arm to provide a vertical force to the horizontal arm, the magnitude and direction of which force is dictated by the optical feedback positioning device. The optical feedback positioning device maintains the second end of the horizontal arm in a fixed vertical position by generating a greater or lesser magnetic force in the coil attached adjacent to the second end of the horizontal arm. The current required to set up the magnetic force provides an accurate measure of the force applied to the float by the thin film, i.e., the surface tension or surface energy of the liquid being investigated. The adjustable weight mechanism located at the first end of the horizontal arm provides a sequence of broad adjustments to the measuring device. In short, the adjustable weight device is adjusted to add or remove thoroughly massive balancing weights as required to keep the magnetic coil within its mechanical operating range. Over the mechanical operating range of the magnetic coil, a highly accurate and sensitive measuring arrangement is provided.

The float according to the invention is of relatively massive construction compared to prior art float designs. The float, which present a barrier at the surface of the substrate is slightly submerged, and may be fixably attached to its vertical support members. This construction prevents swamping of the float during high differential surface tensions, and also simplifies the construction of an effective barrier to first and second substrate portions, in that a flexible ribbon such as Teflon, may be attached to the end walls of the float, since these end walls have appreciable height. The other end of the Teflon ribbon seal is attached to the side walls of the trough so as to prevent the thin film from leaking past the edges of the float.

DESCRIPTION OF THE PREFERRED EMBODIMENT

Figure 1:
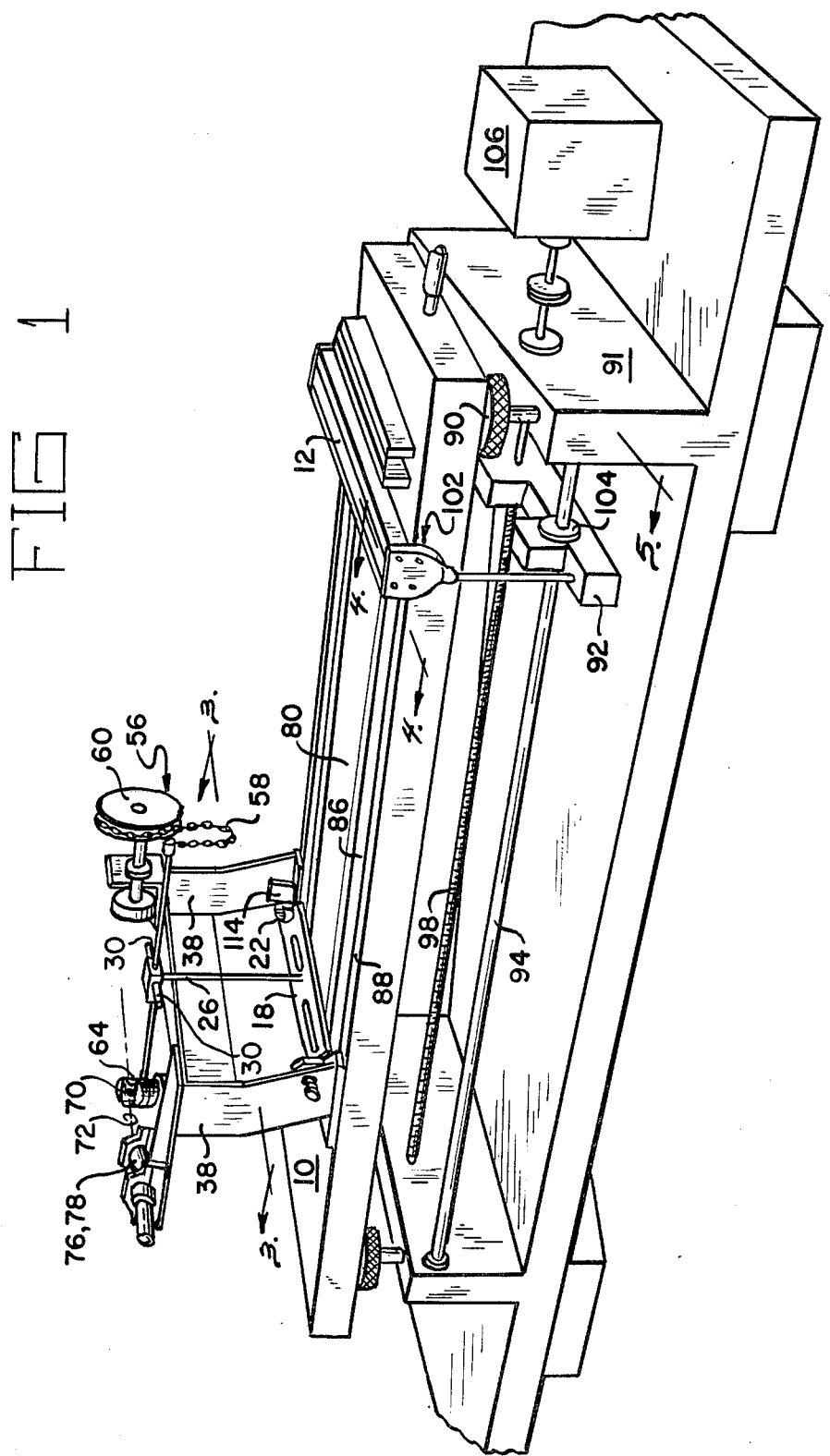
FIG. 1 shows a perspective view of a balance constructed according to the invention.

Referring now to the drawings and especially to FIG. 1, a thin film balance is shown comprising a horizontal trough 10 for holding a liquid substrate, such as clear water. A thin film, such as a monolayer of oil, is floated on the upper surface of the substrate, as is known in the art. Movable barrier 12 is then advanced by motor-driven shaft 98 to compress the thin film by reducing the surface area of the substrate supporting the thin film. The thin film is, in addition to movable barrier 12, bounded by the side walls of trough 10 by a movable float 18, which comprises a portion of balance instrument 20. Float 18 is subjected to a horizontal force as the surface area of the substrate supporting the film is compressed by movable barrier 12. Balance instrument 20 measures this horizontal force on float 18, which provides a measure of the surface energy (surface tension) of the thin film. As described in further detail below, the balance instrument 20 and float 18 are improvements over prior art thin film balances, commonly termed Langmuier type balances.

Figure 2:
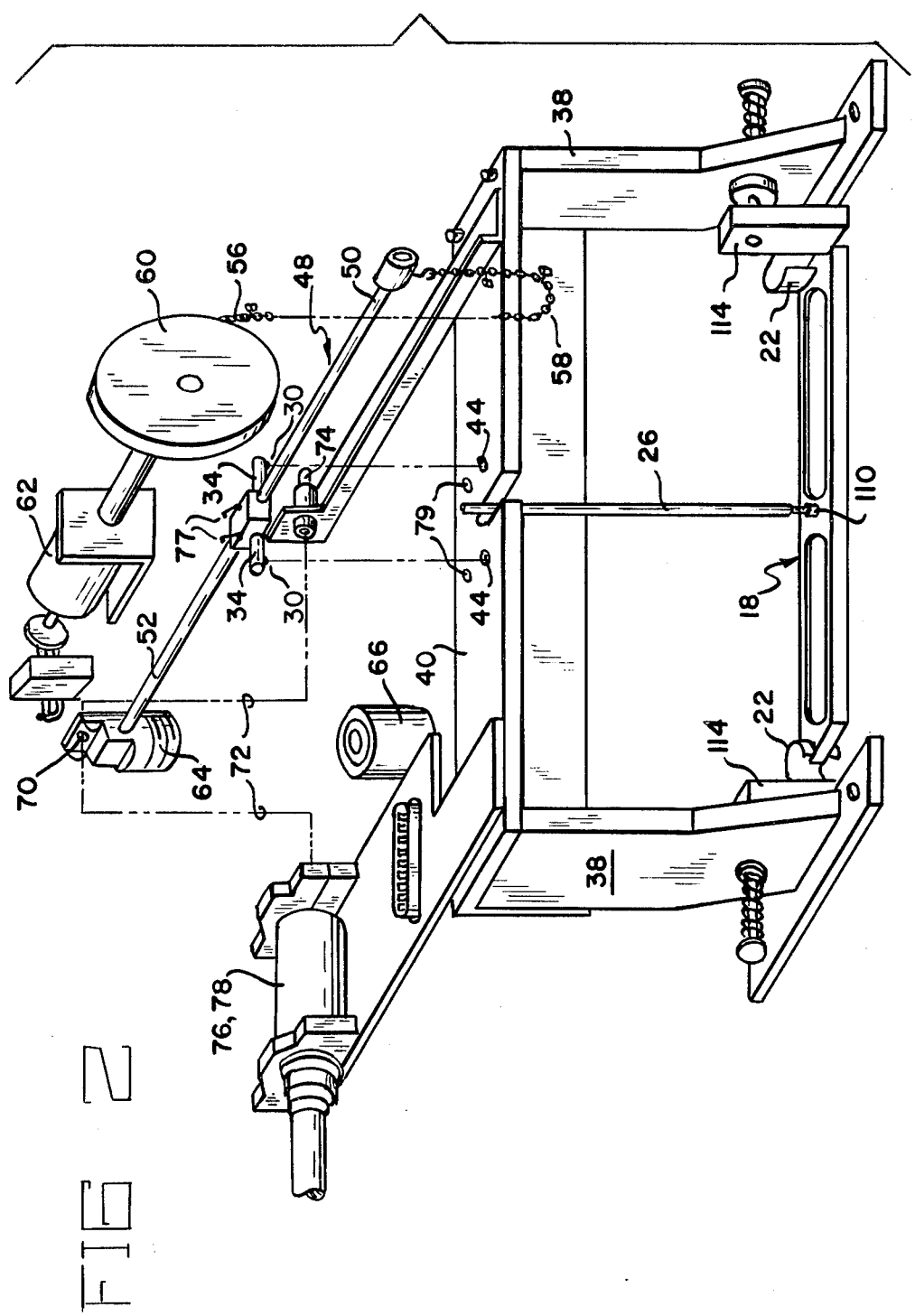
FIG. 2 is an exploded partial view of the balance of FIG. 1, shown in perspective.

Referring now to FIG. 1 and especially to FIG. 2, balance instrument 20 is shown comprising a float 18 which may be of conventional design, but is preferably of the improved design described below. Float 18 floats on the liquid substrate, roughly spanning the width of trough 10. The ends of float 18 are joined to the side walls of trough 10 by sealing means 22, such as flexible ribbons of Teflon or the like. Sealing means 22, along with float 18 present a bounded containment to the thin film, as that film is forced against one side of float 18. Float 18 is connected through vertical support 26 to bearing means 30, which provide a pivotal mounting for float 18. Bearings 30 are as friction free as possible to ensure measurement accuracy, and preferably comprise ruby balls, affixed to cross beam 34. Side walls 38, fixedly secured to trough 10, support horizontal wall 40. Sapphire sockets 44 receive ruby ball bearings 30. A horizontal arm 48 having first and second ends 50, 52 respectively, is fixedly attached to cross beam 34. Horizontal arm 48 is mounted for rotation in a vertical plane which is perpendicular to the substrate surface, and parallel to the side of float 18 which contacts the thin film. A variable weight device 56 is suspended from end 50 of arm 48. Variable weight device 56 comprises a weighted chain 58 fastened to a nylon sheave 60, which is mounted on the shaft of stepping motor 62. An aluminum current conducting coil 64 is mounted on end 52 of shaft 48. Coil 64 is received in permanent magnet 66 and is positioned for movement therewithin in response to horizontal arm 48 pivoting about bearings 30. A lens 70 such as a portion of a chord of Lucite rod is attached to coil 64. Lens 70 is positioned in the optical path, indicated by broken line 72, of an optical feedback mechanism comprising a light source 74, differential photodiode 76, and amplifier means 78. The output of amplifier 78 is fed to an integrating amplifier not shown, which feeds an electric current of appropriate polarity and magnitude to maintain lens 70, (and therefore coil 64), in a fixed horizontal position. Thus, the current in coil 64, and the magnetic field that current produces, balances the force applied to float 18 through the thin film. Should the force on float 18 exceed the magnetic force or should the positional range of coil 64 be exceeded, variable weight mechanism 56 is operated by motor 62 to provide a coarse adjustment to the balance, bringing coil 64 within its operating range. Whereas variable weight mechanism 56 provides a coarse measure of the force on float 18, coil 64 and its associated optical feedback arrangement provides a fine force measurement. In the preferred embodiment, the current to coil 64 is monitored to provide the fine measurement. Monitoring is done by passing the current through a 100 ohm precision resistor, and measuring the voltage drop across the resistor with a precision digital volt meter. One meter unit, equal to 0.1 mv corresponds to approximately 0.9 millidyne/cm of surface pressure. Electrical connection to coil 64 is made through 0.127 mm diameter stainless steel wires 77 which dip into mercury filled cups 79, disposed within horizontal wall 40. Cups 79 are located as close to bearings 30 as possible to avoid any restoring effect impairing the zero and sensitivity of the instrument, caused by wire stiffness.

Referring now to the coarse measurement of variable weight device 56, chain 58, taken from an Ainsworth Chainomatic balance hangs from end 52 of arm 48. A nominal 100 mg weight is fastened to each eighth link of the chain. The arrangement of device 56 was weighed as each weight was added to chain 58, and the incremental value of the added weight was measured to the nearest 0.1 mg.

The deadband of the instrument is determined essentially by the friction in ruby ball bearings 30 and sapphire cups or sockets 44. The absolute accuracy of the instrument is about 30 millidynes/cm compared with a resolution of about one millidyne/cm. This arises because of the slight forward and backward movement permitted by the sockets 44, which changes the position of the light beam on the photodiode. This effect is observed as a zero shift when a single weight is subtracted and then added. If, however, a weight is substracted and then added by pulsing one step beyond the weight and returning to the weight, reproducability is approximately five millidynes/cm.

The electrical system of the balance can almost counter balance the force of device 56 produced by changing two weights, equivalent to about 20 dynes/cm of surface pressure. Over this range, the balance sensitivity of one millidyne/cm has remained constant after numerous disassemblies. It will be noted that the above arrangement enables convenient recalibration of the balance at every experiment.

Referring again to FIG. 2, the novel float design will be described, along with the trough and movable barrier of the preferred embodiment.

Figure 3:
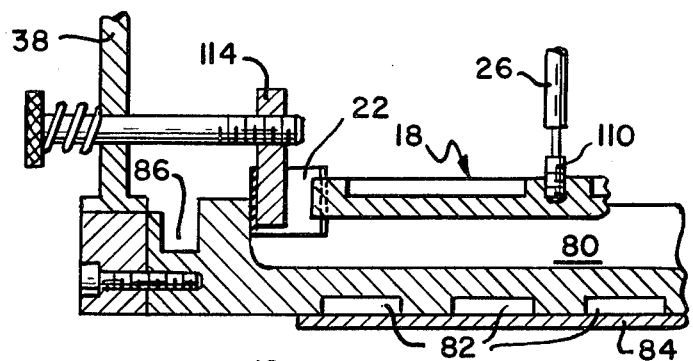
FIGS. 3-5 show cross sectional views of the balance of FIG. 1 taken along lines 3—3, 4—4, and 5—5, respectively.
Figure 4:
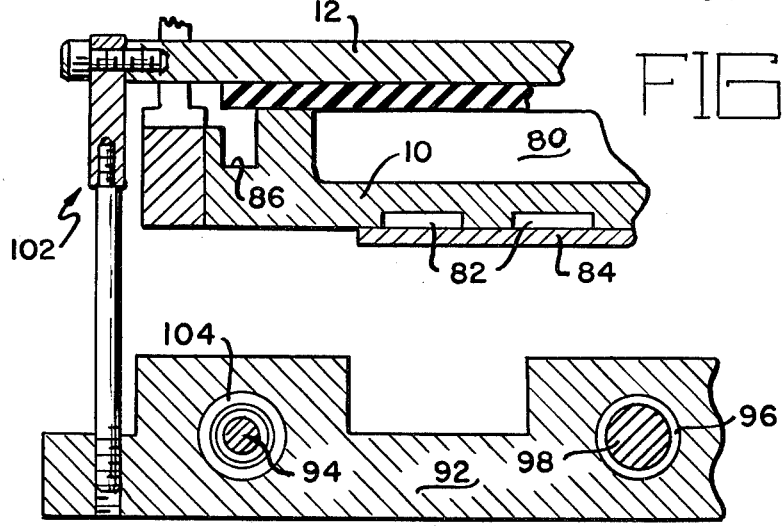
Figure 5:
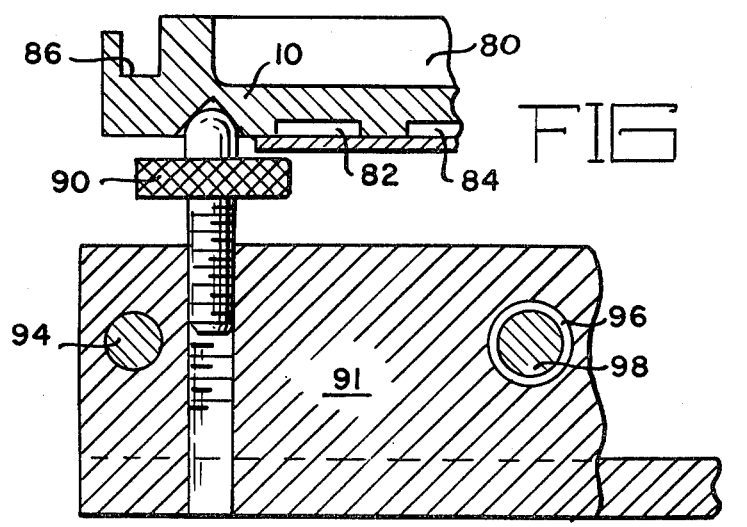

The trough 10 was milled from an aluminum block, 63.5 cm long by 25 cm wide by 2.5 cm thick. Aluminum was selected because of its superior thermalconductivity, ease of fabrication, and low cost. The cross section of the trough is shown in FIGS. 3–5. A liquid cavity 80 was milled so that the depth at one end was 1.3 cm and sloped to 1.6 cm at the other end, in order to facilitate the removal of the water substrate. Channels 82 were milled into the bottom of trough 10 for circulating a temperature regulating fluid, and are sealed by a welded plate 84. A thermocouple well (not shown) was also provided in the bottom of trough 10. The necessary hydrophobic surface was initially provided by a Teflon coating, commercially applied to the interior of trough 10. However, the coating quickly developed pin holes. Water repellency was found to be best obtained by coating the metal with parafin wax between each experiment. A gutter 86 is provided to keep overflows of the substrate from contacting the drive mechanisms. Fastened to the outer edge of the gutters 86 are stainless steel bars 88 which serve as reference rails or surfaces for the balance instrument 20. The gutter edge, as well as the reference rails 88 are 1.6 mm lower than the top of trough 10, in order to eliminate the possibilities of contamination; this construction also makes it possible to bring the movable barrier 12 much closer to float 18. Leveling screws 90 are received in depressions formed in the underside of trough 10 in order to precisely position the trough after disassembly. Pillow blocks 91, located at either end of trough 10, support precision ground guide rods 94 and bearings 96 which provide rotatable support for precision drive screw 98. A carriage 102, on which movable barrier 12 is mounted, is guided by two ball bearing bushings 104 which slide on guide rods 94. The carriage is transported by rotation of precision screw 98. One end of screw 98 is connected to a variable speed motor (not shown), and the other end is connected to an optical shaft encoder 106. The pitch of precision screw 98 and the encoder resolution are selected to produce 800 pulses per linear centimeter of the trough. The motor control was designed to vary the barrier speed in eight discrete steps ranging from 0.05 cm/min to 3.0 cm/min, without the use of mechanical speed reducers. The output of the encoder is fed to an up/down counter with decimal display, so that cumulative counts provide an indication of the barrier position. Three consecutive decimal positions from the counter are converted to an analog voltage which is applied to the X-axis of an X-Y recorder. The analog output range may be selected so that the minimum step on the X-axis is equivalent to either 0.0125 mm or 0.125 mm travel on the barrier. The output of the balance is applied to the Y-axis of the recorder so that a tracing of the surface pressure (differential surface tension) versus surface area of the thin film may be obtained.

Prior art floats had to be light enough to be supported by the surface tension of the substrate, since they were denser than water. Since the floats could not be rigidly attached to the balance, they would tilt as the surface tension of the film decreased, and would sink at high differential pressure. The float 18 constructed according to the invention, shown in FIG. 2, is a substantial departure from conventional floats which suffered from the problems enumerated above. Float 18 is constructed by milling a Kel F block to produce a "boat" having dimensions 13 by 1.27 by 0.635 cm. A pin, 110 preferably made of Kel F is secured in the center of float 18. The weight of the float 18 and pin 110, 7 gm, is low enough so that the assembly is buoyant, independent of surface tension. Pin 110 can slide freely in in the stainless steel tube of the vertical support member 26. Float 18 is prevented from disengagement with vertical support member 26 by a small screw not shown in FIG. 2. Alternatively, float 18 may be fixedly connected to vertical support member 26. Teflon seals or ribbons 22 are attached at one end to float 18 with nylon pins 22 are clamped at their other end to side walls of trough 10 by spring loaded clamps 114. The float and ribbons are immersed in the water substrate, providing liquid-tight seals which prevent leakage of the thin film past float 18. In operation, float 18 is partially submerged in the water substrate. The horizontal force transmitted to float 18 through the thin film is independent of the contact angle of the thin film with respect to the float, and the float has been found to correctly measure surface energy forces.

It can thus be seen that a film balance has been provided that features a wide range of surface tension measurements (80 dynes/cm differential surface tension) at a constant high sensitivity of one millidyne/cm. The film balance, according to the invention, provides increased sensitivity while accommodating optical feedback measuring means. Further, the design of the float, according to the invention, ensures that this sensitivity is maintained over a wide range, even at high differential forces.

We claim:
1. In a horizontal film balance having a receptacle for a liquid substrate upon which a thin film is suspended, a balance instrument comprising:

a float disposed to contact the liquid substrate and the thin film;

means for applying a force to said float through the thin film;

bearing means for mounting said float for movement in response to forces being applied to said float;

a horizontal arm having at least one end portion attached to said bearing means for movement in response to movement of said float;

feedback positioning means for maintaining the end portion of said horizontal arm in a fixed vertical position, said feedback positioning means including force restoring means which balance forces applied to said float; and means for measuring the restoring force.

2. The instrument of claim 1 wherein said bearing means comprise jeweled bearings.

3. The instrument of claim 2 wherein said feedback positioning means comprises an optical path which passes through a lens mounted on the end portion of said horizontal arm.

4. The instrument of claim 2 wherein the force restoring means of said feedback positioning means comprises a current carrying coil in magnetic communication with a magnet.

5. The instrument of claim 4 wherein said means for measuring the restoring force comprises means for measuring the current passing through said coil.

6. The instrument of claim 4 further comprising a variable weight means located adjacent a second end of said horizontal arm for balancing force applied to said float.

7. The instrument of claim 6 wherein said variable weight means comprises a clean scale.

8. The instrument of claim 1 wherein said float comprises an elongated bar spanning substantially the entire distance between opposing walls of the receptacle, said bar having substantial thickness in proportion to its length, at least one million times thicker than the thickness of the thin film, said float lying partially submerged within the liquid substrate.

9. The instrument of claim 8 wherein said float is fixedly secured to said bearing means.

10. The instrument of claim 9 further comprising a movable barrier for compressing the surface area of the liquid substrate upon which the thin film is suspended to thereby apply a force to said float through said thin film.

* * * * *